US005708164A

United States Patent [19]
Winterfeldt et al.

[11] Patent Number: 5,708,164
[45] Date of Patent: Jan. 13, 1998

[54] CEPHALOSTATIN ANALOGUES

[75] Inventors: Ekkehard Winterfeldt, Isernhagen; Andreas Kramer; Ulrike Ullmann, both of Hanover; Henry Laurent, Berlin, all of Germany

[73] Assignee: Schering Aktiengesellschaft, Berlin, Germany

[21] Appl. No.: 564,234

[22] PCT Filed: Jun. 3, 1994

[86] PCT No.: PCT/EP94/01858

§ 371 Date: Jun. 6, 1996

§ 102(e) Date: Jun. 6, 1996

[87] PCT Pub. No.: WO94/29318

PCT Pub. Date: Dec. 22, 1994

[30] Foreign Application Priority Data

Jun. 3, 1993 [DE] Germany .......................... 43 18 924.5

[51] Int. Cl.$^6$ ................................................. C07D 491/22
[52] U.S. Cl. .................................................. 540/9; 540/31
[58] Field of Search ............................................ 540/9, 31

[56] References Cited

PUBLICATIONS

Pettit et al., J. Org. Chem., 1992, 57, pp. 429–431.
Pettit et al., J. Am. Chem. Soc., 1988, 110, pp. 2006–2007.
Smith et al., J. Org. Chem., 1992, 57 pp. 6379–6380.
Kramer et al., J. Chem. Soc., Perkin Trans. 1, 1993, No. 23 p. 2865.
Pan et al., "Synthesis and Pharmacological Evaluation ..." Biorganic & Med. Chem Ltrs. vol. 2, No. 9, pp. 967–972, 1992.
Heathcock et al., "Synthesis and Biological Activity of Unsymmetrical ..." J. Org. Chem. 1994, 59, pp. 6828–6839.

Primary Examiner—Mukund J. Shah
Assistant Examiner—Pavanaram K. Sripada
Attorney, Agent, or Firm—Millen, White, Zelano, & Branigan, P.C.

[57] ABSTRACT

Synthetically produced cephalostatin analogues of the formula I described in the disclosure, synthetic methods for preparing the cephalostatin analogues, pharmaceutical compositions containing the analogues and methods for using the analogues as active agent in pharmaceutical uses, particularly due to their cytotoxic activity.

12 Claims, No Drawings

CEPHALOSTATIN ANALOGUES

This application is a 371 of PCT/EP94/01858.

This invention relates to cephalostatin analogues of general formula I,

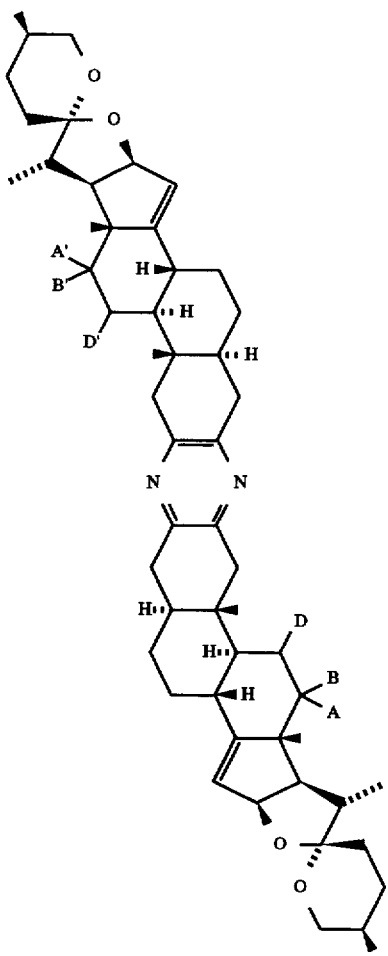

(I)

in which a) A and A' each stand for an alkanoyloxy group R—CO—O— with R as a straight-chain or branched-chain $C_1$ to $C_7$ alkyl radical, and B and D as well as B' and D' each together stand for an additional C—C bond, or b) A' stands for an alkanoyloxy group R—CO—O— with R as a straight-chain or branched-chain $C_1$ to $C_7$ alkyl radical, and B' and D' together stand for an additional C—C bond, and A and B together stand for a keto-oxygen atom and D stands for a hydrogen atom, or c) A stands for a β-position hydroxy group, and B as well as D each stand for a hydrogen atom, and A' and B' together stand for a keto-oxygen atom, and D' stands for a hydrogen atom or d) A and A' each stand for a β-position hydroxy group, and B, D, B' and D' each stand for a hydrogen atom, a process for the production of these cephalostatin analogues, pharmaceutical agents that contain these cephalostatin analogues, and their use for the production of pharmaceutical agents.

BACKGROUND OF THE INVENTION

Cephalostatins represent a group of complex steroidal pyrazine alkaloids, which were isolated from the sea worm *Cephalodiscus gilchristi* ((a) Pettit, G. R.; Kamano, Y.; Dufresne, C..; Inoue, M.; Christi, N.; Schmidt, J. M.; Doubek, D. L.; Can. J. Chem. 1989, 67, 1509. (b) Pettit, G. R.; Inoue, M.; Kamano, Y.; Herald, D. L.; Arm, C.; Dufresne, C.; Christie, N. D.; Schmidt, J. M.; Doubek, D. L.; Krupa, T. S.; J. Am. Chem. Soc. 1988, 110, 2006. (c) Pettit, G. R.; Inoue, M.; Kamano, Y.; Dufresne, C.; Christie, N. D.; Niven, M. L.; Herald, D. L.; J. Chem. Soc., Chem. Commun. 1988, 865. (d) Pettit, G. R.; Kamano, Y.; Inoue, M.; Dufresne, C.; Boyd, R.; Herald, D. L.; Schmidt, J. M.; Doubek, D. L.: Christie, N. D.; J. Org. Chem. 1992, 57, 429). They represent cytotoxins that are highly effective against the PS cell line ($ED_{50}$ $10^{-7}$–$10^{-9}$ µg/ml) and are of potential interest as anti-tumor agents. They are natural marine products that occur rarely, however, and are available only in extremely small amounts. For example, only 139 mg of cephalostatin 1 and a total of 272 mg of other cephalostatins could be isolated from 166 kg of *Cephalodiscus gilchristi* (tubular worms 5 mm long).

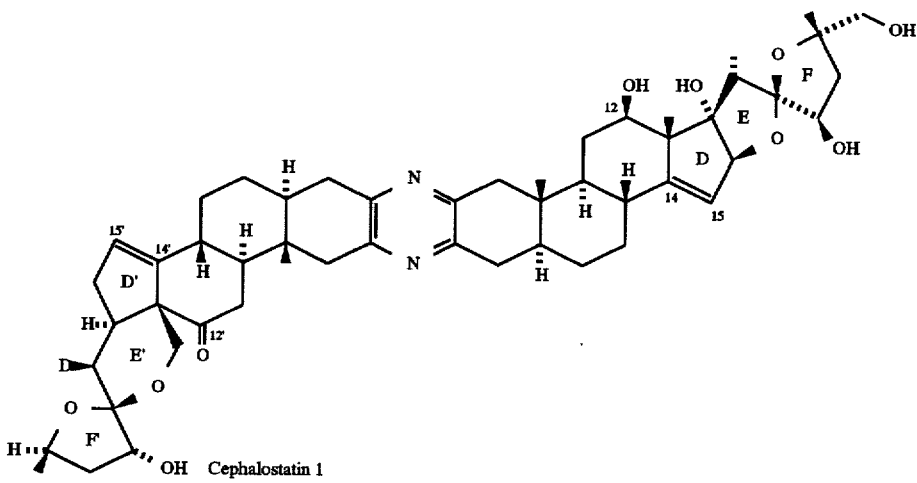

Cephalostatin 1

Cephalostatin 1

Cephalostatin 1 represents an asymmetrically structured and substituted bis-steroidopyrazine, which exhibits a double bond in both the D and D' rings respectively.

Although cephalostatin 7 has become known only recently (Pettit, G. R. et al., loc. cit. (d)), it is a bis-steroidopyrazine that is structured symmetrically relative to the parent substance and is distinguished only by its F and F' rings.

Apart from the very different D-ring substitution, these cephalostatin analogues, furthermore, exhibit neither the 12-hydroxy and 12'-keto or 12-hydroxy functions typical of cephalostatin 1 and cephalostatin 7, nor the double bonds that occur there in the D and D' rings. These double bonds are important for increased solubility of such compounds.

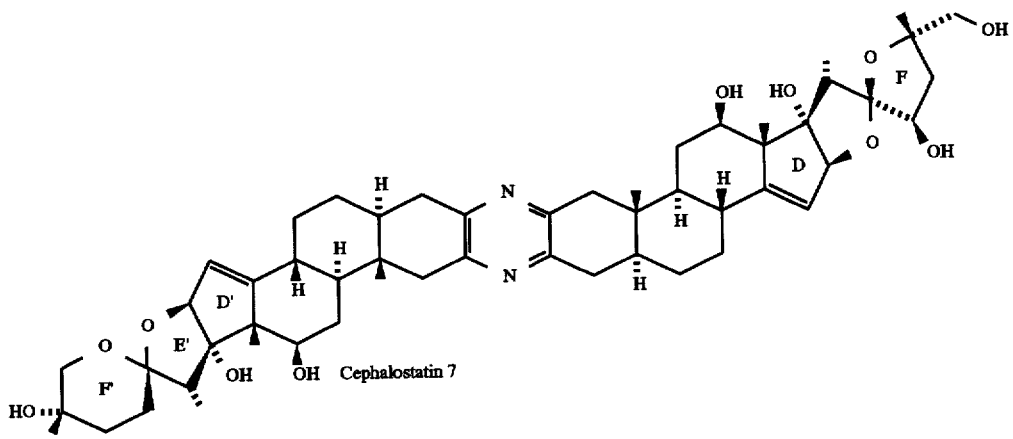

Although cephalostatins belong to the most potent cytotoxins that have ever been screened in the PS system by the National Cancer Institute (USA), in vivo tests are hampered because of the limited availability of natural materials (S.C. Smith and C. H. Heathcock, J. Org. Chem. 1992, 57, 6379). Because of the limited availability, however, there is lively interest in implementing a procedure for total synthesis for cephalostatins. Three processes for forming bis-steroidopyrazines are described by S. C. Smith and C. H. Heathcock (loc. cit.): two of these processes can be used for the production of symmetrical bis-steroidopyrazines in high yields, while the third process makes it possible to synthesize asymmetrical analogues previously known only in the form of naturally occurring cephalostatins.

The cephalostatin analogues that are symmetrical ($R=C_8H_{17}$) or asymmetrical (R=OAc) in structure and can be produced according to said bibliographic references are of the type shown below:

SUMMARY OF THE INVENTION

The object of this invention is to make available naturally occurring cephalostatins, especially cephalostatins 1 and 7, which come as close as possible structurally to cephalostatin analogues and which are capable of being produced according to a simple process that starts from a readily available starting product.

This object is achieved by the provision of compounds of general formula I

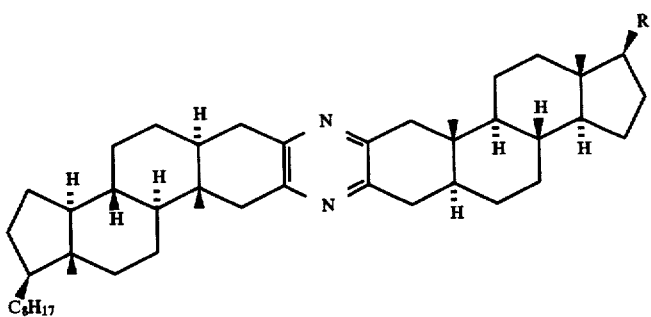

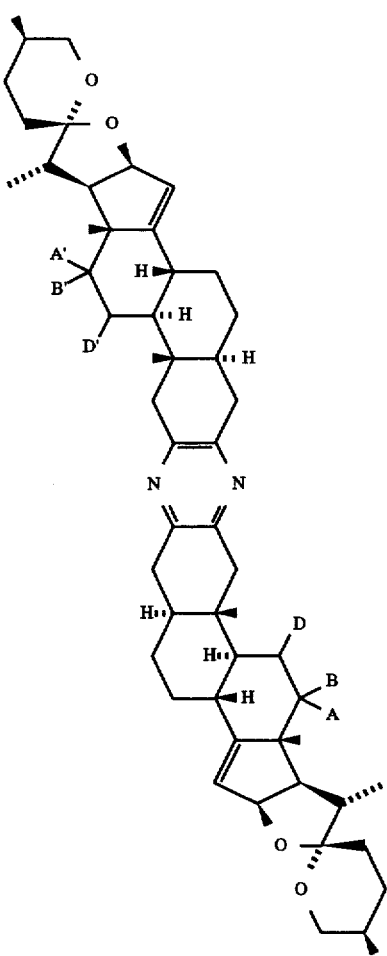

(I)

in which a) A and A' each stand for an alkanoyloxy group R—CO—O— with R as a straight-chain or branched-chain $C_1$ to $C_7$ alkyl radical, and B and D as well as B' and D' each together stand for an additional C—C bond, or b) A' stands for an alkanoyloxy group R—CO—O— with R as a straight-chain or branched-chain $C_1$ to $C_7$ alkyl radical, and B' and D' together stand for an additional C—C bond, and A and B together stand for a keto-oxygen atom, and D stands for a hydrogen atom, or c) A stands for a β-position hydroxy group, and B as well as D each stand for a hydrogen atom, and A' and B' together stand for a keto-oxygen atom, and D' stands for a hydrogen atom, or d) A and A' each stand for a β-position hydroxy group, and B, D, B' and D' each stand for a hydrogen atom.

R—CO— means, for example, an acetyl, propionyl, n-, iso- or tert-butyryl, pivaloyl or valeryl or a higher alkanoyl radical. A pivaloyl radical is preferred for this purpose.

Cases 1c (12β-hydroxy-bis[(25R)-5α-spirost-14-eno][2,3-b;2',3'-e]pyrazin-12'-one) and 1d (bis[(25R)-5α-spirost-14-eno][2,3-b;2',3'-e]pyrazine-12β,12β'-diol) are preferred.

The compounds of formula I exhibit neither a 12-hydroxy function and a 12'-keto function in the same way as cephalostatin 1 nor a 12- and 12'-hydroxy group as well as a 14,15- and 14',15'-double bond in the D- or D'-ring in the same way as cephalostatin 7, which double bond ensures good solubility of the corresponding compounds. The substitution pattern of the D- and D'-rings does not correspond exactly to that of cephalostatin 1 or of cephalostatin 7, but these two rings are also substituted in the same way as in cephalostatin 1 and especially in cephalostatin 7 respectively by a fused spiro system with one oxygen atom each in each ring of the spiro structural element.

It has now been found that the compounds of general formula I according to the invention are highly effective compounds that inhibit cell growth in various human cell lines in the same way as cephalostatin 1.

Owing to their cytotoxic potency, the compounds according to the invention can be used for the production of pharmaceutical agents for the treatment of a wide variety of types of tumors.

This invention thus also relates to the use of the compounds according to the invention for the production of pharmaceutical agents, especially for the treatment and control of carcinomas, sarcomas, and leukemias.

This invention further relates to pharmaceutical preparations that contain at least one compound of general formula I as well as a pharmaceutically compatible vehicle.

The amount of compound(s) to be administered varies within a wide range and can cover any effective amount. Depending on the condition to be treated and the type of administration, the amount of compound administered can be 0.1–50 mg/kg of body weight, preferably 1–30 mg/kg of body weight per day.

Capsules, pills, tablets, coated tablets, etc. are suitable for oral administration. In addition to the active ingredient, the dosage units can contain a pharmaceutically compatible vehicle, such as, e.g., starch, sugar, sorbitol, gelatin, lubricant, silicic acid, talc, etc. The individual dosage units for oral administration can contain, for example, 1 to 100 mg of active ingredient.

For intravenous administration of the compounds according to the invention, their isotonic aqueous solutions are suitable.

Subcutaneous administration of the compounds according to the invention is possible in a solvent such as water and/or polyethylene glycol.

The formulation and administration of the compounds according to the invention can be done analogously to the case of the known cytostatic agents etoposide or methotrexate.

The new compounds of general formula I are produced by the compound of formula II,

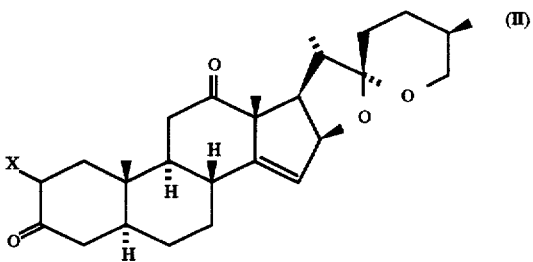

(II)

in which X stands for a bromine atom, being converted by reaction with an alkali azide AlkN$_3$, in which Alk stands for a lithium, sodium or potassium atom, to the compound of formula II, in which X stands for the azide group —N$_3$, by this α-ketoazide being catabolized with heating and nitrogen loss to form 2-imino-3-ketone of formula III

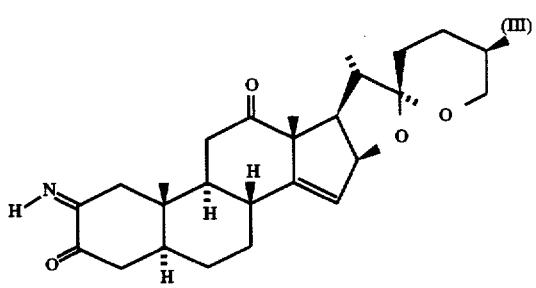

by the latter being dimerized under conditions of catalytic hydrogenation to form symmetrical pyrazinediketone of formula IV, in which R means a straight-chain or branched-chain $C_1$-$C_7$ alkyl radical, or b) this bis-12,12'-keto-steroidopyrazine being reacted by conversion of one of the keto groups in the enolate and its trapping with a compound of general formula V as a $C_2$ to $C_8$ carboxylic acid ester being reacted to form a monoester of general formula Ib,

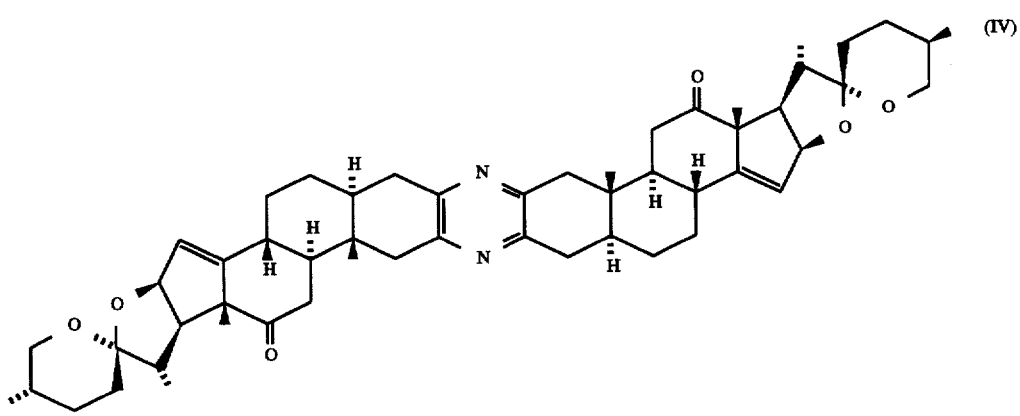

and, if a compound of general formula I is to be produced with substituent definition a), b) or d), a) this bis-12,12'-keto-steroidopyrazine being converted by conversion of both keto groups to the enolate and its trapping as a $C_2$ to $C_8$ carboxylic acid ester with a carboxylic acid chloride or -bromide or a carboxylic anhydride of general formula V, R—CO—Y or (R—CO)$_2$O  (V)

in which

R represents a straight-chain or branched-chain $C_1$ to $C_7$ alkyl radical and Y represents a chlorine or bromine atom, to form a diester of general formula Ia,

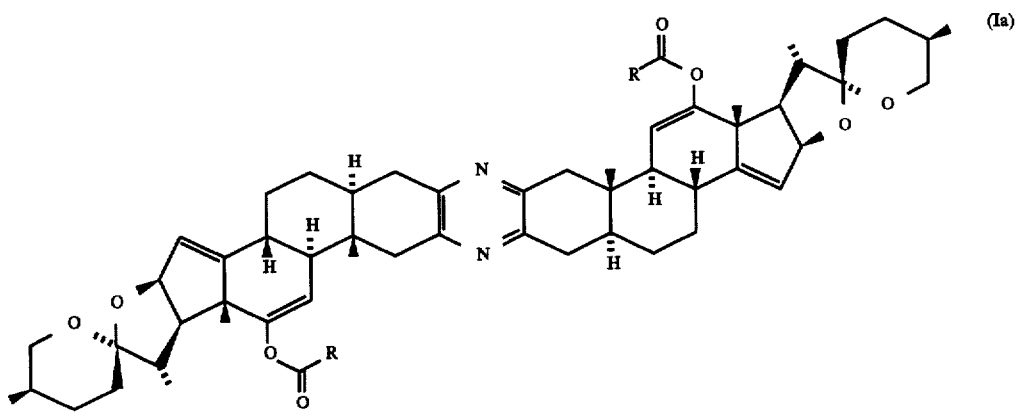

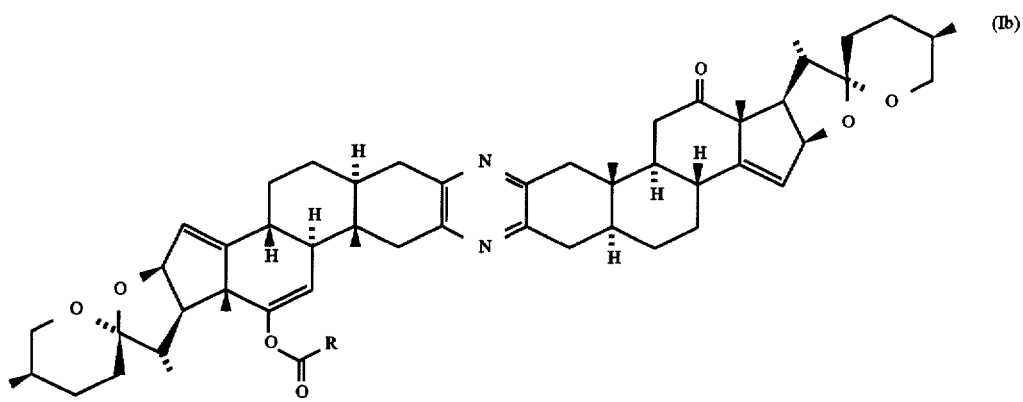

in which R means a straight-chain or branched-chain $C_1$ to $C_7$ alkyl radical, and optionally c) being converted from the 12-keto-12'-alkanoyloxy compound of general formula Ib by reduction of the 12-keto group with an alkali or ammonium borohydride (alkali= lithium, sodium, potassium; ammonium=$NH_4^+$ or $NAlkyl_4^+$, alkyl=$C_1$–$C_4$) and saponification (and tautomerization) of the 12'-ester group to form the compound of formula Ic The above-described process comprises a symmetrical pyrazine synthesis that is simple to implement; the asymmetry that sometimes may ultimately be desired (compound of general formula Ib or Ic) is introduced only in a subsequent reaction step.

As a starting compound of the described process, the $\Delta^{14}$ hecogenin derivative of formula II, in which X represents a

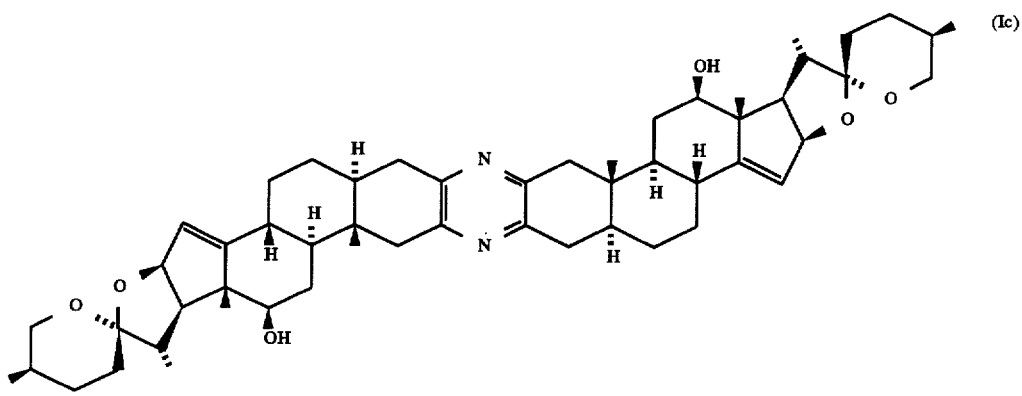

or d) this bis-12,12'-keto-steroidopyrazine being reduced with an alkali or ammonium borohydride (alkali and ammonium cf. Ic) to form bis-12,12'-hydroxy-steroidopyrazine of general formula Id.

bromine atom, is used. The latter is readily accessible from the amply available hecogenin

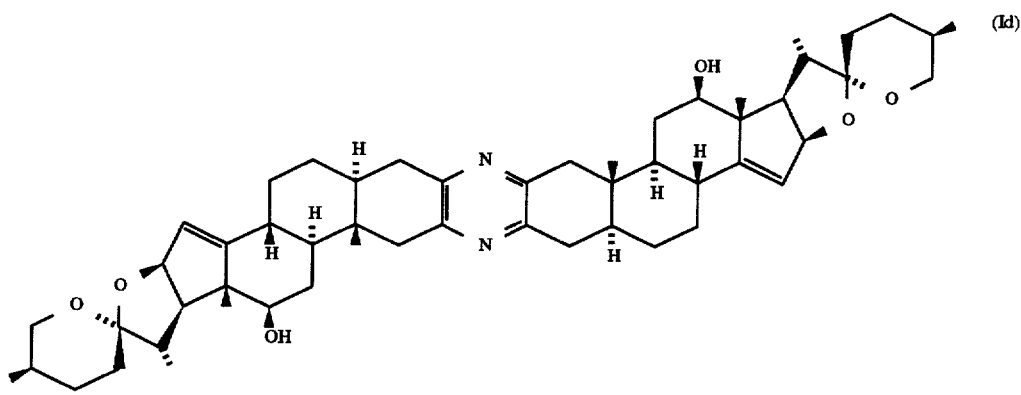

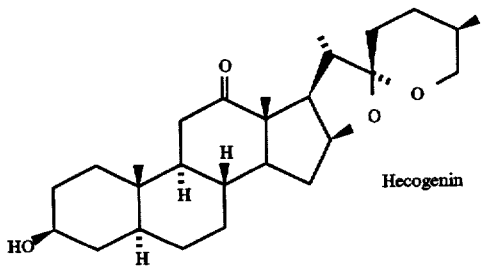

Hecogenin specifically by an established irradiation process with subsequent oxidation and bromation in the 2-position according to the standard process (P. Welzel, B. Janssen, H. Dudek, Liebigs Ann. Chem. 1981, 546).

The subsequent reaction with lithium, sodium or potassium azide, preferably sodium azide (nucleophilic substitution), is carried out in a polar solvent such as dimethylformamide, dimethyl sulfoxide or isopropanol, preferably under the catalytic action of an alkali iodide such as, for example, sodium iodide, at a temperature of 0° to 100° C., for example 50° C.

After working-up with alkaline solution, the iminoketone III is obtained in a very good yield (up to 90%), which as such does not tend toward pyrazine formation. Under conditions of catalytic hydrogenation (palladium [10%] on activated carbon, hydrogenation at room temperature), however, symmetrically structured precursor IV spontaneously forms the cephalostatin analogues of general formula I that are ultimately to be produced. As a solvent, a polar solvent, such as, for example, ethyl acetate with the addition of a small amount of an alcohol, for example, methanol, is used here. The reaction is tracked by thin-layer chromatography. After working-up and chromatography, pyrazine IV is obtained in a likewise good yield of about 65%.

This invention also relates to the pyrazinediketone of formula IV as an intermediate product.

In a cover-gas atmosphere by proton trapping with an excess of sodium or potassium hexamethyldisilazane, the corresponding dienolate or monoenolate is then produced from pyrazinediketone IV, which by trapping with a carboxylic acid chloride or -bromide or a carboxylic anhydride of general formula V, $$R—CO—Y \text{ or } (R—CO)_2O \quad (V)$$

in which

R represents a straight-chain or branched-chain $C_1$ to $C_7$ alkyl radical and Y represents a chlorine or bromine atom, is stabilized as a dicarboxylic or monocarboxylic acid ester of general formula Ia or Ib.

The enolates are trapped preferably with pivaloyl chloride and stabilized as pivalates.

The production and trapping of enolates is carried out in dry ethereal solution, for example, in tetrahydrofuran.

Whether preferably the dienolate or the monoenolate is formed depends on, i.a., the level of the excess of the enolizing agent sodium or potassium hexamethyldisilazane: a large excess of over 4 equivalents results first of all and predominantly in dienolate; after trapping, for example, as pivalate, a mixture of bis-enolpivalate 1a and asymmetrical monopivalate Ib that is desired in this case is obtained.

When using 3 to 3.5, preferably 3.2 equivalents of the enolizing agent potassium hexamethyldisilazane and trapping as pivalate, an approximately 1:2 mixture of bis-enolpivalate 1a and the desired asymmetrical mono-pivalate 1b is obtained. Separation of it can be done in a simple way by column chromatography. Although, owing to the symmetrical structure of the pyrazinediketone used, the reaction can result not only in monoenolate and monoenolester, monoenolester Ib is still ultimately obtained in a considerable yield of 40%.

Whether preferably the monoenolate or dienolate and the corresponding ester results depends, in addition to the basic excess, also on the reaction time and the amount of the acid halide (pivaloyl chloride) or acid anhydride offered for trapping the enolate that is formed. The cephalostatin analogue of general formula Ie is finally formed from monoenolester Ib by borohydride reduction (lithium, sodium, potassium boronate or an ammonium boronate) and subsequent saponification of the enolester group and tautomerization of the enol into ketone. The substitution pattern of the steroid rings of this hydroxyketone corresponds to the situation found in naturally occurring cephalostatin 1.

Reduction is done preferably with sodium or tetrabutylammonium boronate, specifically in a solution of dichloromethane and methanol at temperatures below −50° C., for example, at −78° C. (dry ice/acetone). After several hours of stirring, the reaction is halted by adding acetone. After working-up, the enolester is saponified according to usual processes, for example in dichloromethane solution with 10 equivalents of potassium hydroxide that has been dissolved in a little water. After several hours of refluxing, the reaction is halted by adding citric acid. After working-up and chromatography on silica gel, cephalostatin analogue 1c is obtained in a very good yield (80%).

The following example is used for a more detailed explanation of the invention.

EXAMPLE

2-Bromo-(25R)-5α-spirost-14-ene-3,12-dione (II)

500 mg of (25R)-5a-spirost-14-ene-3,12-dione is dissolved in 15 ml of tetrahydrofuran and mixed with 453 mg (1.1 eq) of pyridinium bromide-perbromide, dissolved in 25 ml of tetrahydrofuran. After two and one half hours of stirring at room temperature, the reaction is arrested by adding 20 ml of water and the mixture is extracted with dichloromethane. The organic phase is washed with sodium chloride solution, dried on magnesium sulfate, the solvent is removed and the residue is chromatographed with petroleum ether/ethyl acetate (4:1) on silica gel. The combined fractions are concentrated by evaporation and stirred overnight in 10 ml of methanol. After filtration and evaporation of the solvent, there is obtained:

409 mg (70%) of α-bromide and 111 mg (19%) of a mixture of α- and β-bromide;

MS (FAB) α-bromide (m/c): 507 ($M^+$+2);

$^1$H-NMR (200 MHz, $CDCl_3$, δ): 5.48 tr, J=2 Hz, 15-H (1); 4.76 dd, J=2 Hz 8 Hz, 16α-H (1); 4.72 dd, J=6 Hz 14 Hz, 2β-H (1); 3.50 m, i.a., $CH_2$-27, (4); 1.32 s, $CH_3$-18 (3); 1.21 s, $CH_3$-19 (3); 1.05 d, J=7 Hz, $CH_3$-21 (3); 0.81 d, J=6 Hz, $CH_3$-26 (3).

2-Imino-(25R)-5α-spirost-14-ene-3,12-dione (III)

500 mg (0.99 mmol) of 2-bromo-(25R)-5α-spirost-14-ene-3,12-dione (II) is dissolved in 50 ml of dimethylformamide. After adding 700 mg of sodium azide and a few milligrams of sodium iodide, the solution is stirred for 2 hours at 50° C. The reaction mixture is brought to room temperature, poured into 20 ml of water and extracted with methyl-tert-butyl ether. This extract is washed with saturated sodium chloride solution, dried on magnesium sulfate and concentrated by evaporation. After crystallization, 407 mg (80%) of iminoketone III is obtained.

MS (m/c): 439 (M⁺);

¹H-NMR (200 MHz, CD₂Cl₂, δ): 5.86 s,=N-H (1); 5.41 tr, J=Hz, 15-H (1); 4.71 dd, J=2 Hz 8 Hz, 16α-H (1); 3.34 m, i.a., CH₂-27 (4); 1.30 s, CH₃-18 (3); 1.10 s, CH₃-19 (3); 1.01 d, J=7 Hz, CH₃-21 (3); 0.79 d, J=6 Hz, CH₃-26 (3).

Bis[(25R)-5α-spirost-14-eno][2,3-b;2',3'-e]pyrazine-12,12'-dione (IV)

897 mg (2.04 mmol) of iminoketone III is dissolved in 50 ml of ethyl acetate and mixed with 3 ml of methanol and 5 drops of acetic acid. After adding 270 mg of palladium-carbon (10%), it is hydrogenated at room temperature (TLC control). After the reaction is completed, it is filtered, the filtrate is washed with saturated sodium bicarbonate solution and saturated sodium chloride solution, dried on magnesium sulfate and concentrated by evaporation. The residue is chromatographed with petroleum ether/ethyl acetate (2:1) on silica gel and after crystallization, pyrazine IV is obtained in a yield of 64%.

MS (FAB, m/c): 845.5 (M⁺):

¹H-NMR (200 MHz, CDCH₃, δ): 5.49 s, br, (2); 4.78 dd, J=2 Hz 8 Hz (2); 3.44 m, i.a., CH₂-27 (6); 1.33 s, (6); 1.04 d, J=7 Hz, (6); 0.92 s, (6); 0.80 d, J=6 Hz (6).

12'-Pivaloyloxy-bis[(25R)-5α-spirost-14-eno][2,3-b;2',3'-e]pyrazin-11'en-12-one (Compound of general formula Ib)

100 mg of pyrazine diketone IV is dissolved under argon in 7 ml of absolute tetrahydrofuran and then 3.2 equivalents of potassium hexamethyldisilazane is added at room temperature. After 30 minutes, it is mixed with 0.16 ml of pivaloyl chloride and stirred for 15 hours at room temperature. The solution is then poured into cold aqueous citric acid and extracted with methyl-tert-butyl ether. The extract is washed with saturated sodium bicarbonate solution and with saturated sodium chloride solution, dried on magnesium sulfate, concentrated by evaporation and chromatographed on silica gel. 44 mg (40%) of monopivalate 1b is obtained in this way.

MS (FAB, m/c): 929.7 (M⁺);

¹H-NMR (200 MHz, CDCl₃, δ): 5.49 m, (2); 5.21 s, hr., (1); 4.81 dddd, J=2 Hz 8 Hz (2); 3.45 m, i.a., CH₂-27,27' (6); 1.33 s (3); 1.28 s (9); 1.22 s, (3); 1.05 dd, J=7 Hz (6); 0.92 s (3); 0.89 s (3); 0.80 d, J=6 Hz (6).

12β-Hydroxy-bis[(25R)-5α-spirost-14-eno][2,3-b;2',3'-e]pyrazin-12'-one (1c)

(Reduction of monoenolester 1b and release of 12-keto-12'-hydroxy compound 1c)

63 mg (0.0678 mmol) of monopivalate Ib is dissolved in 8 ml of solvent (dichloromethane/methanol 1:1) and mixed at −78° C. with 5 mg (4 eq) of sodium boranate. After 3 hours of stirring at −78° C., it is quenched with 1.5 ml of acetone, the mixture is brought to room temperature, diluted with dichloromethane, washed with 1M NaOH solution, dried on magnesium sulfate, the solvent is removed and the residue is chromatographed on silica gel (petroleum ether/ethyl acetate 1:1). Examination of the reaction product is done based on the IR spectrum. The subsequent saponification of the enolester takes place in dichloromethane/methanol (1:1) with 10 eq of KOH, dissolved in a little water. After 6 hours of refluxing, it is cooled to room temperature, quenched with diluted citric acid, and the mixture is extracted with dichloromethane. After the organic extract is washed with diluted sodium bicarbonate and sodium chloride solution, it is dried on magnesium sulfate, the solvent is removed and the residue is chromatographed on silica gel (petroleum ether/ethyl acetate 1:1). Yield relative to Ib: 78%.

MS (FAB, m/c): 847.6 (M⁺);

¹H-NMR (200 MHz, CD₂Cl₂, δ): 5.42 tr, J<1 Hz (1); 5.37 tr, J<1 Hz (1); 4.83 dd, J=2 Hz 8 Hz (1); 4.73 dd, J=2 Hz 8 Hz (1); 3.36 m, (6); 1.31 s (3); 1.01 d, J=7 Hz (6); 1.01 s (3); 0.90 s (3); 0.85 s (3); 0.80 d, J=6 Hz (6).

Bis[(25R)-5α-spirost-14-eno][2,3-b;2',3'-e]pyrazine-12β,12β'-diol (Id)

110 mg of pyrazine diketone IV (0.13 mmol) is dissolved in about 10 ml of dichloromethane and mixed with 134 mg (4 eq=0.5206 mmol) of tetrabutylammonium borohydride and stirred for 4 hours at room temperature. To arrest the reaction, the reaction mixture is mixed with 2N citric acid solution. The aqueous phase is separated and extracted several times with dichloromethane. The combined organic phases are washed with diluted sodium bicarbonate solution and saturated sodium chloride solution, dried on magnesium sulfate and concentrated by evaporation on a rotary evaporator. For purification, it is chromatographed on silica gel with petroleum ether/ethyl acetate (1:1). 56 mg (0.0659 mmol=50.6% yield) of diol Id is obtained.

We claim:

1. A cephalostatin analogue of formula I,

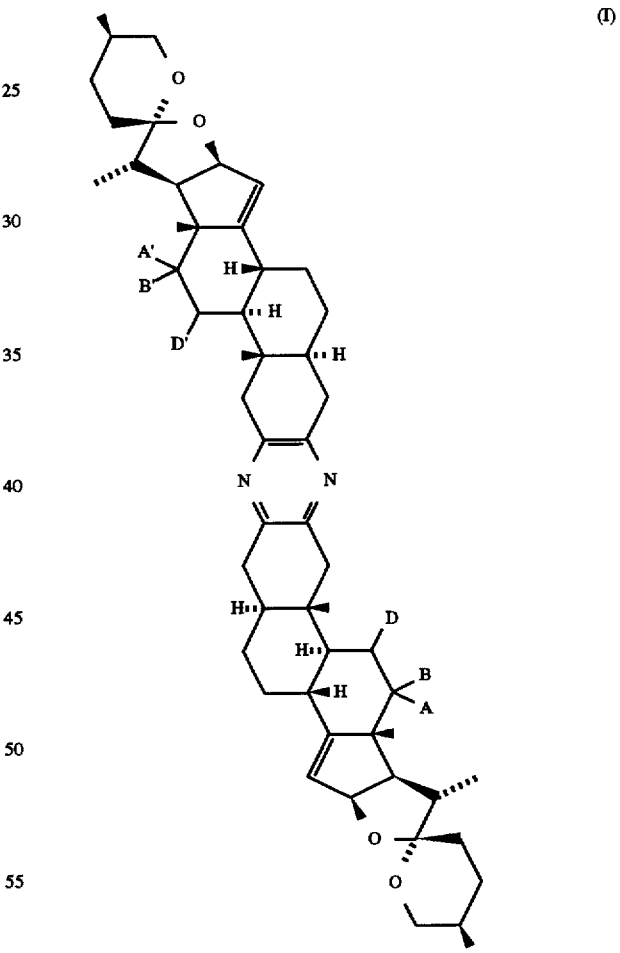

(I)

in which a) A and A' each stand for an alkanoyloxy group R—CO—O— with R as a straight-chain or branched-chain C₁ to C₇ alkyl radical, and B and D as well as B' and D' each together stand for an additional C—C bond, or b) A' stands for an alkanoyloxy group R—CO—O— with R as a straight-chain or branched-chain C₁ to C₇ alkyl radical, and B' and D' together stand for an additional C—C bond, and A and B together stand for a keto-oxygen atom and D stands for a hydrogen atom, or c) A stands for a β-position hydroxy group, and B as well as D each stand for a hydrogen atom, and A' and B' together stand for a keto-oxygen atom, and D' stands for a hydrogen atom or d) A and A' each stand for a β-position hydroxy group, and B, D, B' and D' each stand for a hydrogen atom.

2. A cephalostation analogue of formula I of claim 1, which is 12β-Hydroxy-bis[(25R)-5α-spirost-14-eno][2,3-b;2',3'-e]pyrazin-12'-one; or bis[(25R)-5α-spirost-14-eno][2,3-b; 2',3'-e]pyrazine-12β,12β'-diol.

3. A process for the production of a cephalostatin analogue of formula I according to claim 1, which comprises converting a compound of formula II,

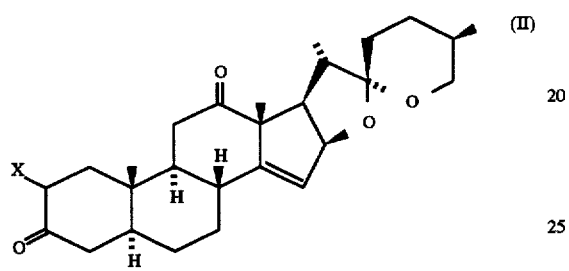

in which X stands for a bromine atom, by reaction with an alkali azide, AlkN$_3$, in which Alk stands for a lithium, sodium or potassium atom, to an α-ketoazide compound of formula II, in which X stands for the azide group, —N$_3$, catabolizing this α-ketoazide with heating and nitrogen loss to form 2-imino-3-ketone of formula III

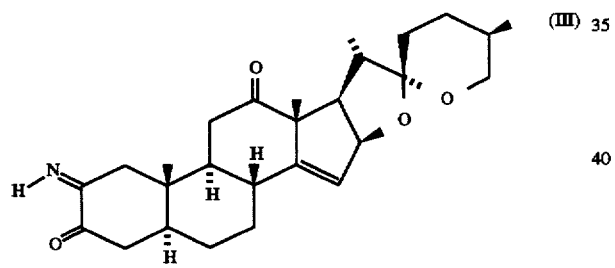

dimerizing the 2-imino-3-ketone under conditions of catalytic hydrogenation to form symmetrical bis-12,12'-ketosteroidopyrazine of formula IV, a) for a compound according to part a) of formula I, converting this bis-12,12'-ketosteroidopyrazine, by conversion of both keto groups to the enolate and its trapping as a $C_2$ to $C_8$ carboxylic acid ester with a carboxylic acid chloride or -bromide or a carboxylic anhydride of formula V, $$R\text{—}CO\text{—}Y \text{ or } (R\text{—}CO)_2O \qquad (V)$$

in which

R represents a straight-chain or branched-chain $C_1$ to $C_7$ alkyl radical and Y represents a chlorine or bromine atom, to form a diester of formula Ia,

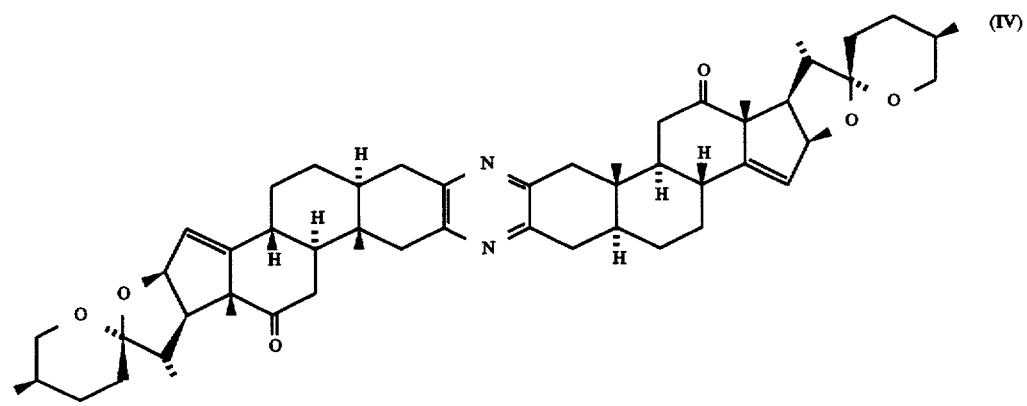

and,

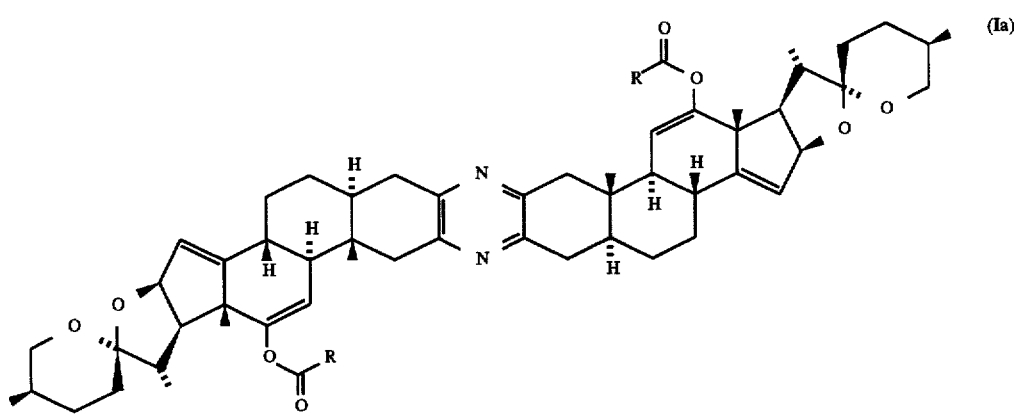

(Ia)

in which R means a straight-chain or branched-chain $C_1$–$C_7$ alkyl radical, or b) for a compound according to part b) of formula I, reacting the bis-12,12'-ketosteroidopyrazine, by conversion of one of the keto groups in the enolate and its trapping with a compound of formula V as a $C_2$ to $C_8$ carboxylic acid ester, to form a monoester of formula Ib, of the 12-keto group with an alkali or ammonium borohydride and saponification of the 12'-ester group, to form the compound of formula Ic

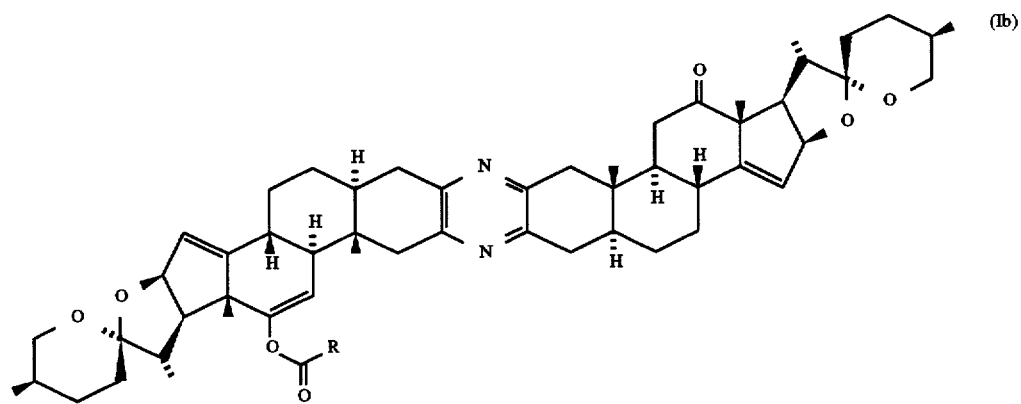

(Ib)

in which R means a straight-chain or branched-chain $C_1$ to $C_7$ alkyl radical, or

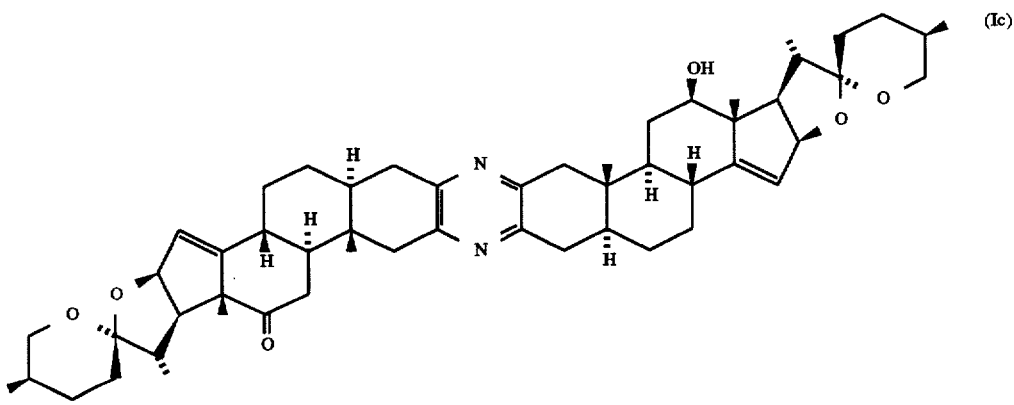

(Ic)

c) for a compound according to part c) of formula I, converting the compound of formula Ib, by reduction d) for a compound according to part d) of formula I, reducing the bis-12,12'-ketosteroidopyrazine with an alkali or ammonium borohydride to form bis-12,12'-hydroxysteroidopyrazine of formula Id

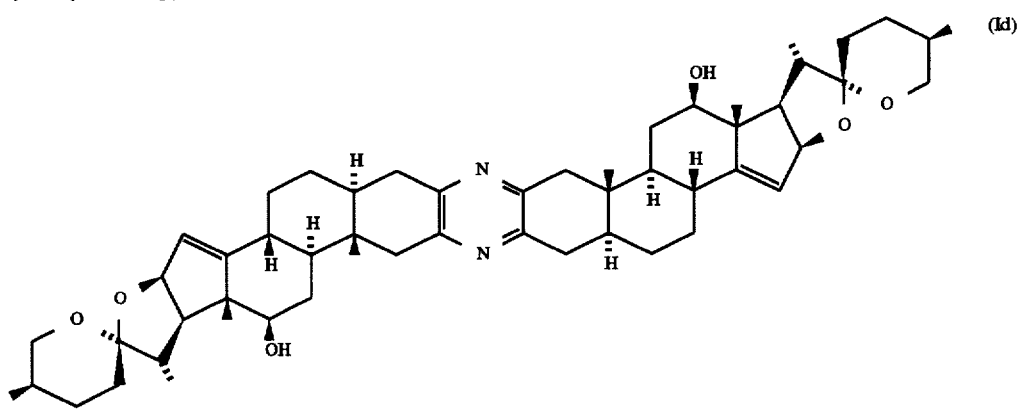

4. An intermediate compound of formula IV

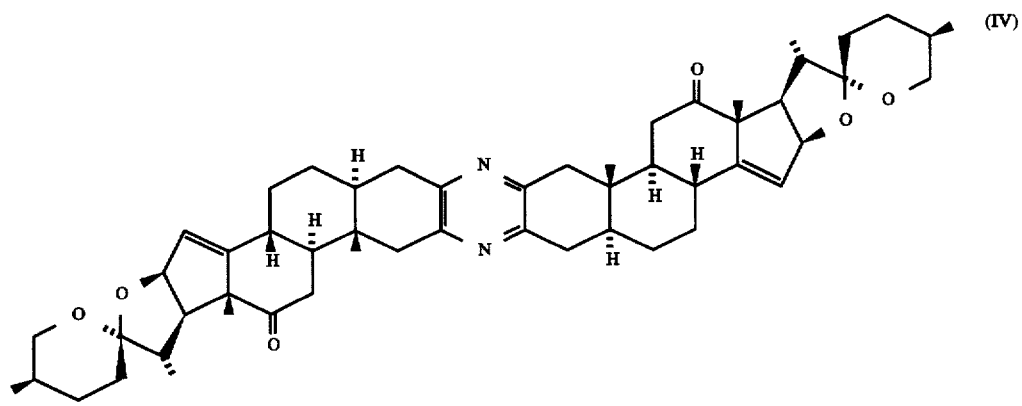

5. A pharmaceutical composition comprising at least one cephalostatin analogue of formula I according to claim 1 and a pharmaceutically compatible vehicle therefor.

6. A method for inhibiting cell growth in a human cell line which comprises administering an effective amount of a cephalostatin analogue of the formula I of claim 1.

7. A method for cytotoxic treatment of tumors which comprises administering a cytotoxic effective amount of a cephalostatin analogue of the formula I of claim 1.

8. The method of claim 6, wherein the cephalostatin analogue is administered in an amount of 0.1 to 50 mg/kg of body weight per day.

9. The method of claim 7, wherein the cephalostatin analogue is administered in an amount of 0.1 to 50 mg/kg of body weight per day.

10. The process of claim 3, wherein the alkali or ammonium borohydride used in process variants c) or d) is lithium, sodium or potassium borohydride or $NH_4^+$ or $N(alkyl)_4^+$ borohydride, where alkyl is $C_1$–$C_4$.

11. A cephalostatin analogue according to formula I of claim 1, which is produced synthetically.

12. A cephalostatin analogue according to formula I of claim 1, prepared by converting a compound of formula II,

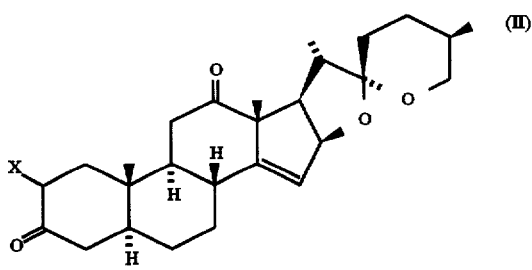

in which X stands for a bromine atom, by reaction with an alkali azide, $AlkN_3$, in which Alk stands for a lithium, sodium or potassium atom, to an α-ketoazide compound of formula II, in which X stands for the azide group, —$N_3$, catabolizing this α-ketoazide with heating and nitrogen loss to form 2-imino-3-ketone of formula III

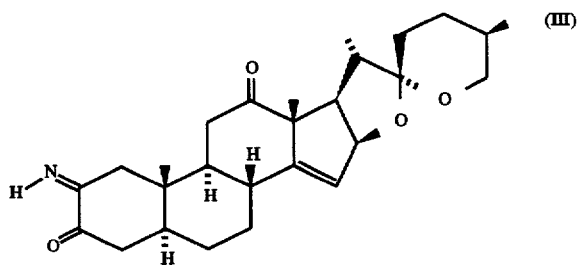

dimerizing the 2-imino-3-ketone under conditions of catalytic hydrogenation to form symmetrical bis-12,12'-ketosteroidopyrazine of formula IV, b) for a compound according to part b) of formula I, reacting the bis-12,12'-ketosteroidopyrazine, by conversion of one of the keto groups in the enolate and its

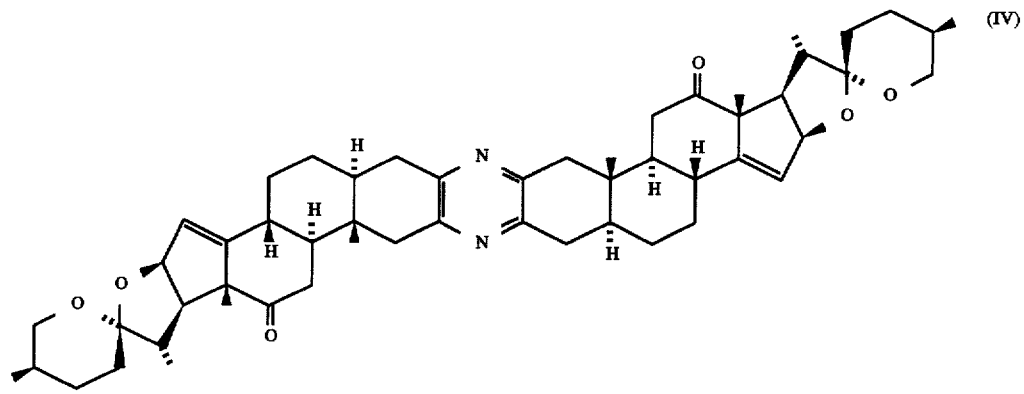

and, a) for a compound according to part a) of formula I, converting this bis-12,12'-ketosteroidopyrazine, by conversion of both keto groups to the enolate and its trapping as a $C_2$ to $C_8$ carboxylic acid ester with a carboxylic acid chloride or -bromide or a carboxylic anhydride of formula V, trapping with a compound of formula V as a $C_2$ to $C_8$ carboxylic acid ester, to form a monoester of formula Ib,

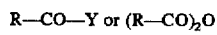

R—CO—Y or (R—CO)$_2$O    (V)

in which

R represents a straight-chain or branched-chain $C_1$ to $C_7$ alkyl radical and Y represents a chlorine or bromine atom, to form a diester of formula Ia,

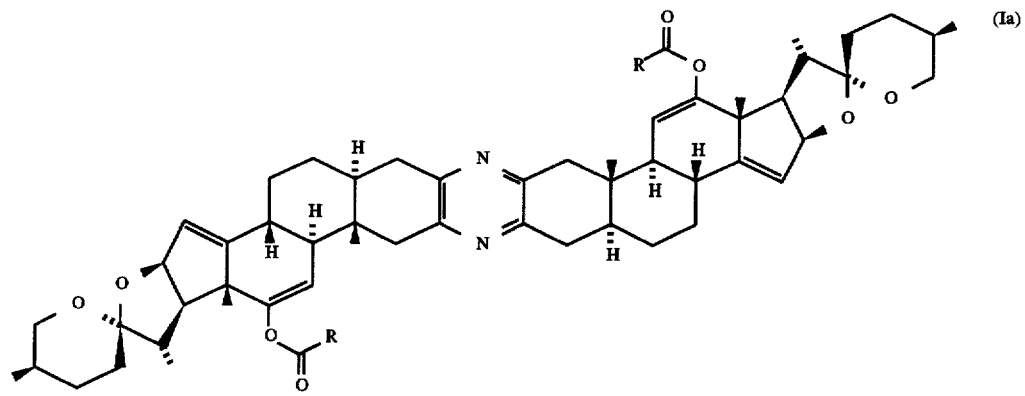

in which R means a straight-chain or branched-chain $C_1$–$C_7$ alkyl radical, or

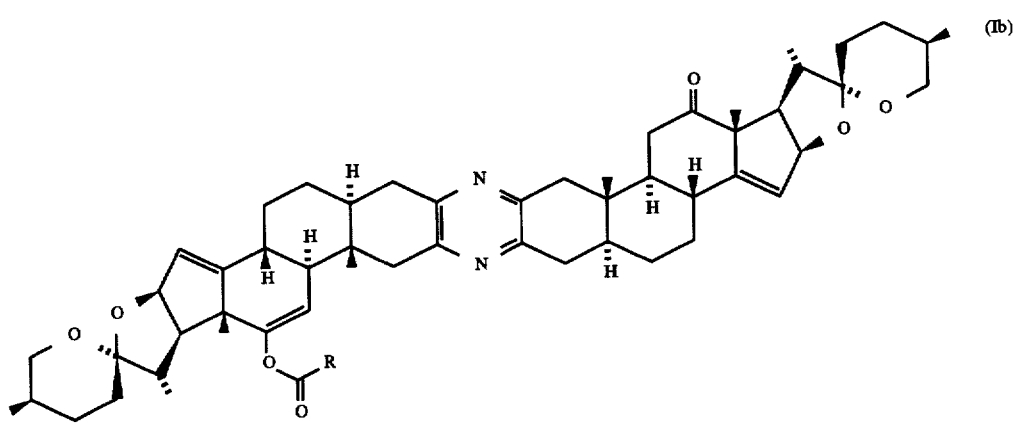

in which R means a straight-chain or branched-chain $C_1$ to $C_7$ alkyl radical, or c) for a compound according to part c) of formula I, converting the compound of formula Ib, by reduction of the 12-keto group with an alkali or ammonium borohydride and saponification of the 12'-ester group, to form the compound of formula Ic

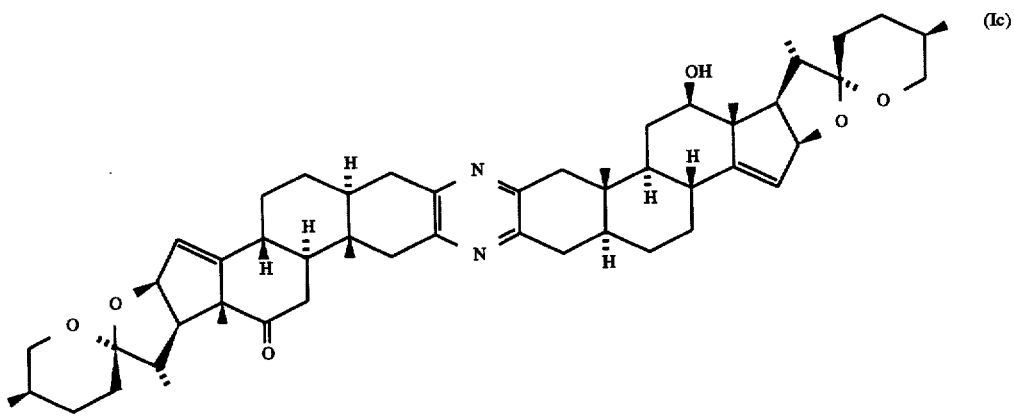

or d) for a compound according to part d) of formula I, reducing the bis-12,12'-ketosteroidopyrazine with an alkali or ammonium borohydride to form bis-12,12'-hydroxysteroidopyrazine of formula Id

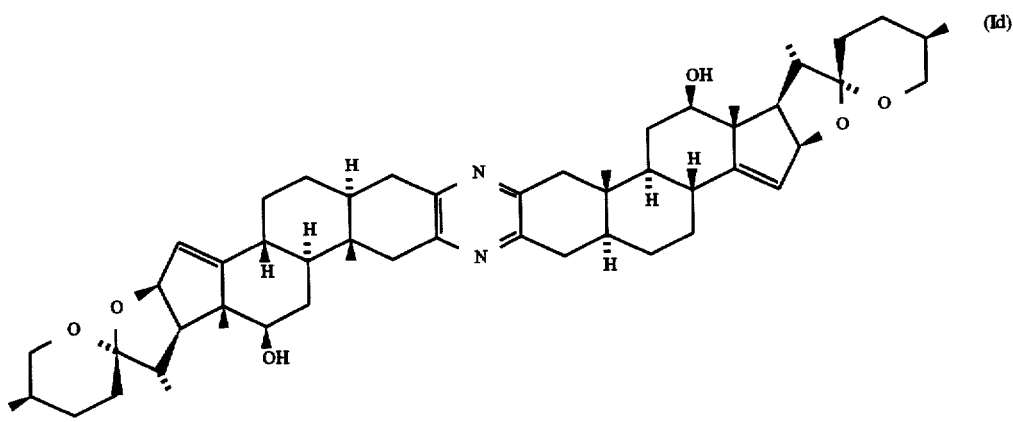

* * * * *